(12) United States Patent
Rockey et al.

(10) Patent No.: US 9,522,138 B2
(45) Date of Patent: Dec. 20, 2016

(54) SYSTEMS, METHODS, TECHNIQUES, AND COMPOUNDS IN RESEARCH AND TREATMENT OF PORTAL HYPERTENSION AND OTHER CONDITIONS (71) Applicants: Don C. Rockey, Charleston, SC (US); Songling Liu, Charleston, SC (US); Glenn Cornett, New York City, NY (US)

(72) Inventors: Don C. Rockey, Charleston, SC (US); Songling Liu, Charleston, SC (US); Glenn Cornett, New York City, NY (US)

( * ) Notice: Subject to any disclaimer, the term of this patent is extended or adjusted under 35 U.S.C. 154(b) by 0 days.

(21) Appl. No.: 14/588,391

(22) Filed: Dec. 31, 2014

(65) Prior Publication Data
US 2015/0182510 A1    Jul. 2, 2015

Related U.S. Application Data (60) Provisional application No. 61/922,797, filed on Dec. 31, 2013.

(51) Int. Cl.
*A61K 31/44* (2006.01)
*A61K 31/4355* (2006.01)

(52) U.S. Cl.
CPC .................................. *A61K 31/4355* (2013.01)

(58) Field of Classification Search
None
See application file for complete search history.

(56) References Cited

U.S. PATENT DOCUMENTS 4,383,998 A * 5/1983 Esanu ................... C07D 491/04
514/302
5,026,855 A * 6/1991 Bonato ................ C07D 491/04
546/116

OTHER PUBLICATIONS

Medline 1994 327918.*

* cited by examiner

*Primary Examiner* — Heidi Reese
(74) *Attorney, Agent, or Firm* — Jones IP Group (57) ABSTRACT Methods and compounds for research and treatment of portal hypertension. The use of racemic or non-racemic mixtures of furopyridine isomers to stimulate eNOS function in sinusoidal endothelial cells and to increase NO production in both normal sinusoidal endothelial cells and injured endothelial cells.

5 Claims, 9 Drawing Sheets

SYSTEMS, METHODS, TECHNIQUES, AND COMPOUNDS IN RESEARCH AND TREATMENT OF PORTAL HYPERTENSION AND OTHER CONDITIONS

BACKGROUND OF THE INVENTION

Field of the Invention

The present invention relates to systems, methods, techniques, and compounds having numerous applications including in research and treatment of portal hypertension and other conditions.

Description of the Related Art

The endothelium plays a central role in the maintenance of vascular homeostasis largely by virtue of its synthesis of nitric oxide (NO). It is now well appreciated that the endothelial isoform of nitric oxide synthase (eNOS) produces endothelium-derived NO. Furthermore, endothelial dysfunction contributes to the development and clinical course of vascular diseases such as pulmonary and portal hypertension, both characterized by reduced NO bioactivity.

(±)3-(4-Chlorophenyl)-1,3-dihydro-7-hydroxy-6-methyl-furo-(3,4-c)pyridine 3-(4-chlorophenyl)-1,3-dihydro-7-hydroxy-6-methylfuro-(3,4-c)pyridine (cicletanine), a substituted synthetic pyridine developed as an antihypertension agent, has been shown to exert direct relaxant effects on vascular smooth muscle.

We have unexpectedly found that cicletanine has or may have a direct effect on eNOS activity in sinusoidal endothelial cells. We have discovered and demonstrated that cicletanine increases nitric oxide synthase (NOS) activity and NO production in both normal sinusoidal endothelial cells and injured endothelial cells, in part via protein kinase B (Akt) and MAP kinase/Erk signaling. Furthermore, paracrine NO regulates stellate cell contractility and appears to reduce portal pressure.

SUMMARY OF THE INVENTION

The function of the endothelial isoform of nitric oxide synthase (eNOS) and production of nitric oxide (NO) is altered in a number of disease states. Pharmacological approaches to enhancing NO synthesis and thus perhaps endothelial function could have substantial benefits in patients. We analyzed the effect of cicletanine, a synthetic pyridine with potent vasodilatory characteristics, on eNOS function and NO production in normal (liver) and injured rat sinusoidal endothelial cells, and we studied the effect of cicletanine-induced NO on stellate cell contraction and portal pressure in an in vivo model of liver injury. Sinusoidal endothelial cells were isolated from normal and injured rat livers. After exposure to cicletanine, eNOS phosphorylation, NO synthesis, and the signaling pathway regulating eNOS activation were measured. Cicletanine led to an increase in eNOS ($Ser^{1177}$) phosphorylation, cytochrome c reductase activity, L-arginine conversion to L-citrulline, as well as NO production. The mechanism of the effect of cicletanine appeared to be via the protein kinase B (Akt) and MAP kinase/Erk signaling pathways. Additionally, cicletanine improved NO synthesis in injured sinusoidal endothelial cells. NO production induced by cicletanine in sinusoidal endothelial cells increased protein kinase G (PKG) activity as well as relaxation of stellate cells. Finally, administration of cicletanine to mice with portal hypertension induced by bile duct ligation led to reduction of portal pressure. We have discovered that cicletanine improves eNOS activity in injured sinusoidal endothelial cells and activates hepatic stellate cell NO/PKG signaling. Our unexpected discoveries suggest and we posit that cicletanine therapies can improve intrahepatic vascular function in portal hypertensive patients.

The present invention also comprises methods, systems, techniques, and compounds, for treating portal hypertension with cicletanine through direct action on the liver vascular bed. This is unexpected because, to date, no hypertension agents have been demonstrated to lower portal blood pressure through direct action on the liver vascular bed. While some agents decrease blood flow into the liver, these represent a suboptimal therapy which does not get directly at the problem of vascular dysfunction in the liver itself.

Furthermore, the present inventor has demonstrated that the (+) isomer (S isomer) of cicletanine was more effective than the (−) isomer of cicletanine as to production of nitrite, which in turn is involved in cicletanine's purported mechanism of action in portal hypertension. This is again unexpected, as it is in direct contradistinction to vasorelaxant effects found in pulmonary arteries.

DETAILED DESCRIPTION

Aspects of the present invention are illuminated by the following Example, Figures, and Discussion.

PRESENTATION OF EXAMPLES

Example 1

Materials and Methods

Cell isolation and culture. Sinusoidal endothelial cells were isolated from male Sprague-Dawley rats (450-500 g) (Harlan, Indianapolis, Ind.). In brief, after in situ perfusion of the liver with 20 mg/100 mg pronase (Roche Molecular Biochemicals, Indianapolis, Ind.), followed by collagenase (Worthington Biochemical, Lakewood, N.J.), dispersed cell suspensions were removed from a layered discontinuous density gradient of 8.2 and 15.6% Accudenz (Accurate Chemical and Scientific, Westbury, N.Y.), further purified by centrifugal elutriation (18 ml/min flow), and were grown in medium containing 20% serum (10% horse/calf). The purity of endothelial cells was documented by their uptake of fluorescently labeled di-I-acetoacetylated low-density lipoprotein as described (21). Only primary sinusoidal endothelial isolates of >95% purity were used for study. Experiments were performed with cells from a minimum of three different isolations (for all experiments).

For coculture experiments, freshly isolated stellate cells and freshly isolated sinusoidal endothelial cells were isolated separately and mixed together on collagen-coated plates and cultured for 5 days. Sinusoidal endothelial cells were plated at a density of 200,000 cells/cm2, and stellate cells were at a density of 65,000 cells/cm2.

Adenovirus. Adenovirus (Ad) control empty vector (Ad-EV), constitutively active Akt (Ad-myrAkt), and dominant-negative Akt (Ad-dnAkt) have been described in "A Crucial Role for GRK2 in Regulation of Endothelial Cell Nitric Oxide Synthase Function in Portal Hypertension" *Nat Med* 11: 952-958, 2005 by Liu, Premont, Kontos, Zhu, and Rockey ("Liu"). Sinusoidal endothelial cells were exposed to Ad in 2% serum for 16 h, and medium was exchanged; cells were then harvested at the specified time points.

Immunoblotting. Immunoblotting was performed by using specified primary antibodies, including anti-eNOS antibody (1:1,000; BD Transduction Laboratories, San Jose, Calif.), anti-phospho-eNOS-Ser$^{1177}$ (1:1,000; BD Transduction Laboratories or Cell Signaling Technology), anti-phospho-Akt, anti-Akt (Cell Signaling Technology, Beverly, Mass.), and horseradish peroxidase-conjugated secondary antibody. Specific signals were visualized using enhanced chemiluminescence as per the manufacturer's instructions and were scanned and quantitated with standard software.

Animal model of liver injury and portal hypertension. Liver injury and portal hypertension were induced by performing bile duct ligation in 450- to 500-gram male retired breeder Sprague-Dawley rats as described in Liu and 20- to 25-gram male BALB/c mice. Briefly, bile duct ligation was performed by surgical isolation and ligation of the common bile duct. This model creates a portal-based fibrogenic response and portal hypertension 10-14 days after surgery (Liu). For study of injured sinusoidal endothelial cells, we used the rat model of bile duct ligation (10-14 days post-surgery); for in vivo study (primarily to conserve the use of active compound), we used the mouse model of bile duct ligation (examining portal pressure 4 wk postsurgery). In sham-operated rats or mice, laparotomy without isolation and section of the bile duct was performed. Studies were approved by the local Institutional Animal Care and Use Committees. Portal pressure measurement. Portal hypertension was induced in male BALB/c mice by bile duct ligation as above. Cicletanine (5 mg·kg$^{-1}$·day$^{-1}$) or vehicle was given by gavage as a single daily dose for 10 days before portal pressure measurement as described in Liue. In brief, mice were anesthetized, and an intravenous catheter (Becton Dickinson Vascular Access, Sandy, Utah) was introduced in the portal vein and secured with a silk tie. A calibrated low-pressure transducer (Digi-Med, Louisville, Ky.) was connected to the portal vein catheter, and portal pressure was recorded continuously using the Digi-Med Integrator 200 System (Digi-Med).

NO Measurement.

To assess NO production, we analyzed the release of nitrite, the stable breakdown product of NO, using a nitrite/nitrate assay kit (Cayman Chemicals, Ann Arbor, Mich.), following the manufacturer's instructions. Briefly, conditioned medium from sinusoidal endothelial cells with or without cicletanine treatment were loaded on a 96-well plate and mixed with both enzyme cofactor and nitrate reductase. After incubation at room temperature for 3 h, 100 µl Griess reagent mix were added to each well. After 10 more minutes at room temperature, the absorbance of each well was determined on a microplate reader at 540 nm, and the nitrite concentrations were deduced from a standard curve.

NOS Activity Assay.

NOS activity from sinusoidal endothelial cell lysates was assessed by measuring the conversion of L-[3H]arginine to L-[3H]citrulline as described (6) per the manufacturer's instructions (Cayman Chemical). In brief, triplicate samples of cell lysates were incubated with a reaction buffer containing 3 pmol of L-[3H]arginine (45 Ci/mmol), 0-50 µM arginine, 1 mM NADPH, 100 nM calmodulin (CaM), 2 mM CaCl2, and 30 µM BH4 in a volume of 50-100 µl at room temperature for 30 min and at 37° C. for an additional 30 min in the presence and absence of 1 mM NG-nitro-L-arginine methyl ester (L-NAME). The reaction mixture was terminated by the addition of stop buffer and passed over a Dowex AG 50WX-8 resin column. Radiolabeled counts per minute of generated L-citrulline were measured and used to determine L-NAME-inhibitable NOS activity (thus, each experiment included total counts and background counts). Cytochrome c reductase assay. The reductase activities of sinusoidal endothelial cells with or without cicletanine exposure were determined using the NADPH-dependent cytochrome c assay. The reaction was carried out in a total volume of 1.1 ml containing cell lysates (30 µg) in 50 mM Tris.HCl, pH 7.2, 1 µM CaM, 0.2 mM CaCl2, manganese superoxide dismutase (Mn-SOD, 400 U/ml), and 100 µM cytochrome c. The reaction was initiated by the addition of NADPH to a final concentration of 0.5 mM. The reduction of cytochrome c was monitored at 550 nm at 25° C. (Beckman Spectrophotometer-Model DU650). Mn-SOD (400 U/ml) was included to eliminate the cytochrome c reduction contributed by $O_2$. The linear portion of the kinetic traces was used to calculate the rate of cytochrome c reduction and reductase activity of eNOS. Turnover number was calculated using the absorbance change during this 30-s interval and an extinction coefficient of 0.021/µM.

Collagen lattice assay. Contraction of hepatic stellate cells was performed as previously described with minor modifications (25). Briefly, individual wells of a 24-well culture dish were incubated with PBS containing 1% BSA (500 µl/well) for 1 h at 37° C. and then washed two times with PBS and allowed to air dry. Collagen gels were prepared by mixing 60% type I tail collagen (Upstate Laboratories), 10% 10×MEM (GIBCO), 10% 0.2 HEPES, and 20% DMEM (GIBCO) to make a final concentration of collagen of 2.4 mg/ml. The solution was added to the culture wells and incubated for 1 h at 37° C., and hepatic stellate cells and sinusoidal endothelial cells were isolated separately from normal rat livers and cocultured (each at a density of 100,000 cells/lattice) on collagen lattices for 5 days. Cells were changed to serum-free medium overnight, then exposed to cicletanine, and then stimulated with endothelin-1 (ET-1, 10 nM). Collagen lattices were released from their substrata, and gel contraction was measured from 0 to 30 min.

Statistical Analyses.

All experiments were performed in replicate using cells isolated from different rats. All results were expressed as means+/−SE. We performed statistical analysis using the two-tailed Student's t-test, and P<0.05 was considered statistically significant.

Results

Cicletanine Stimulates eNOS in Sinusoidal Endothelial Cells.

Figure 1:
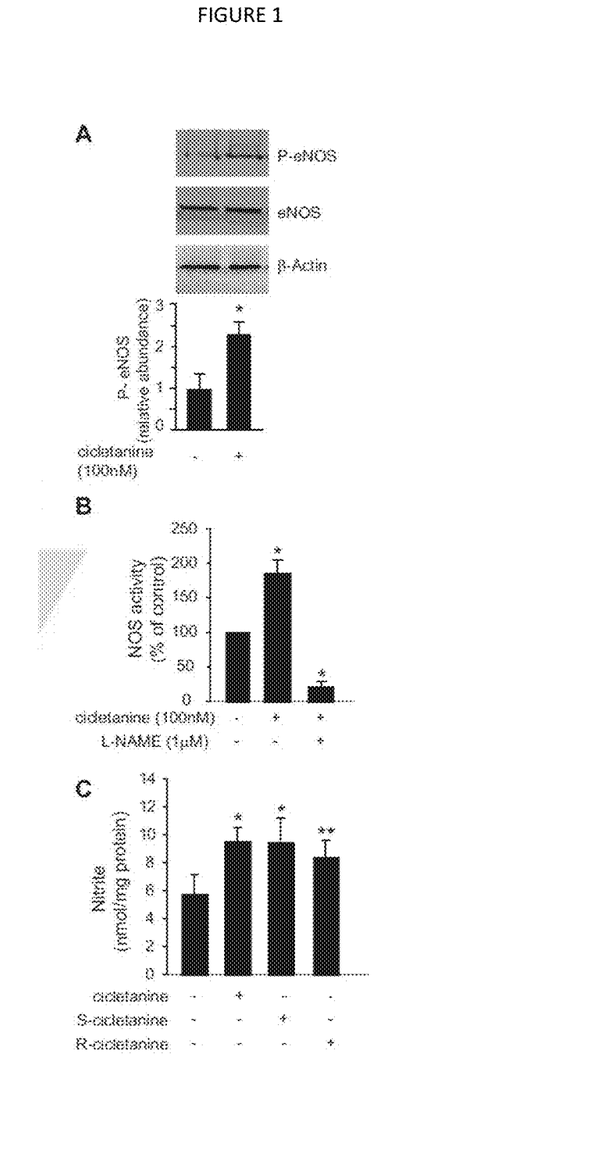
FIG. 1 comprises charts and graphics showing the effect of cicletanine on the function of endothelial isoform of nitric oxide synthase (eNOS) in sinusoidal endothelial cells.

We examined whether cicletanine is capable of activating eNOS in sinusoidal endothelial cells; since eNOS is typically phosphorylation dependent, we initially examined eNOS phosphorylation (Ser$^{1177}$). After exposure to cicletanine (100 nM), total eNOS expression was unchanged, whereas phosphorylation at Ser$^{1177}$ was stimulated (FIG. 1A). Consistent with eNOS phosphorylation and activation, exposure of sinusoidal endothelial cells to cicletanine (100 nM) led to robust eNOS activity (i.e., conversion of arginine to citrulline), inhibitable by LNAME (FIG. 1B). In addition, nitrite levels in conditioned medium were significantly increased after exposure to cicletanine, S-cicletanine, or R-cicletanine (FIG. 1C), consistent with the results of phosphorylation and citrulline activity assays.

FIG. 1 shows the effect of cicletanine on the function of endothelial isoform of nitric oxide synthase (eNOS) in sinusoidal endothelial cells. A: sinusoidal endothelial cells were isolated from rat livers and exposed to cicletanine (100 nM) for 2 h, cell lysates were harvested, and phosphor (P)-eNOS (Ser$^{1177}$), total eNOS, and _-actin were detected by immunoblotting. In the graph shown on the bottom, bands corresponding to phospho-eNOS were quantified (n=4, *P<0.01 vs. control). B: the activity of nitric oxide synthase (NOS) in normal sinusoidal endothelial cells was examined in the same cells. NOS activity without exposure to cicletanine was arbitrarily set to 100; n=3, *P<0.01 vs. control (no cicletanine), **P<0.01 vs. cicletanine. L-NAME, NG-nitro-L-arginine methyl ester. C: cells were treated with cicletanine, S-cicletanine, and Rcicletanine as indicated for 2 h, conditioned medium was harvested, and nitrite levels were measured as in MATERIALS AND METHODS (n=3, *P<0.001 and **P<0.05 vs. control).

Cicletanine Induces eNOS Activity in a Time- and Dose Dependent Manner.

Figure 2:
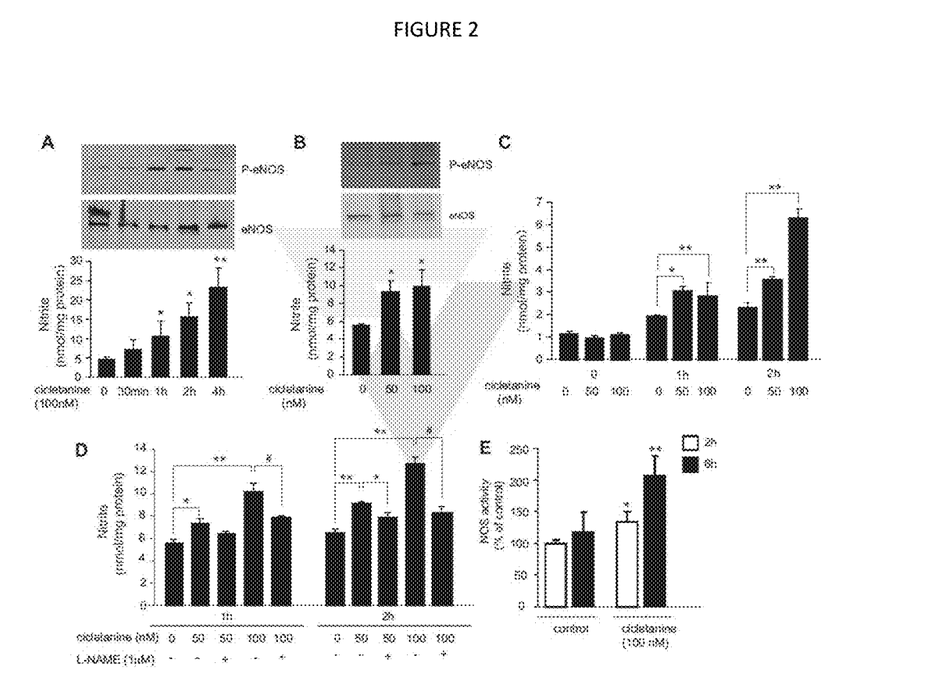
FIG. 2 comprises charts and graphics showing cicletanine induced eNOS activity in a time- and dose-response manner.

We next investigated the effect of cicletanine at different times after its exposure to sinusoidal endothelial cells. We exposed sinusoidal endothelial cells to cicletanine (100 nM) for 0-4 h before harvesting cells and conditioned medium (FIG. 2A). Cicletanine's effects on nitrite production were also dose dependent (FIG. 2B). Cicletanine induced eNOS phosphorylation to the greatest extent at 1 h after exposure; nitrite levels started to increase at 30 min and continued to accumulate over time (FIG. 2, A and C). The NOS inhibitor L-NAME inhibited nitrite production (FIG. 2D). To determine the extent to which cicletanine increased eNOS activity above the basal level, we collected cell lysates at 2 and 6 h after exposure to cicletanine (100 nM) and measured NOS activity. Cicletanine led to consistent increases in eNOS activity at both time points; these increases were greater at 6 h (FIG. 2E).

FIG. 2 shows cicletanine induced eNOS activity in a time- and dose-response manner. A: sinusoidal endothelial cells were isolated from rat livers and exposed to cicletanine (100 nM) from 1 to 4 h, and cell lysates were subjected to immunoblotting to detect phosphor- or total eNOS. Blots shown are representative of 3 others. In the lower panel, nitrite levels were measured in conditioned medium form the same cells, and quantitative data are shown in the graph below. Medium from cells without treatment served as a control (n=3, *P<0.05 and **P<0.01 vs. time "0"). B: sinusoidal endothelial cells were exposed to 50 or 100 nM cicletanine for 2 h, and cell lysates were subjected to immunoblotting to detect phosphor- or total eNOS. Blots shown are representative of 3 others. In the lower panel, nitrite levels were measured in conditioned medium from the same cells, and quantitative data are shown in the graph below; medium from cells without treatment served as a control (n=3, *P<0.01 vs. control). C: normal sinusoidal endothelial cells were exposed to indicated concentrations of cicletanine, and nitrite was measured in conditioned medium at the indicated times; medium from cells without treatment served as controls (n=3, *P<0.01 and **P<0.05 vs. control). D: normal sinusoidal endothelial cells were preexposed to L-NAME (1 μM) or not for 4 h and then exposed to the cicletanine (at the indicated concentrations) for a further 1 or 2 h. In the upper panel is shown a representative immunoblot of cell lysates. Conditioned medium was collected, and nitrite levels were measured as in MATERIALS AND METHODS (n=3, *P<0.05 vs. 1-h control, **P=0.01 vs. 2-h control, *P<0.01 indicates significant difference between indicated groups). E: sinusoidal endothelial cells were exposed to cicletanine (100 nM) for either 2 or 6 h, cells were harvested, and NOS activity was measured in cell lysates, which was normalized to the level observed at the 2-h time point without cicletanine (n=3, *P<0.05 vs. 2-h exposure control, **P<0.001 vs. 6-h exposure controls).

Increased eNOS activity caused by cicletanine can be attributed to enhanced reductase activity. We found a significant increase in cytochrome c reductase activity after exposure of sinusoidal endothelial cells to cicletanine (100 nM) (FIG. 3).

Figure 3:
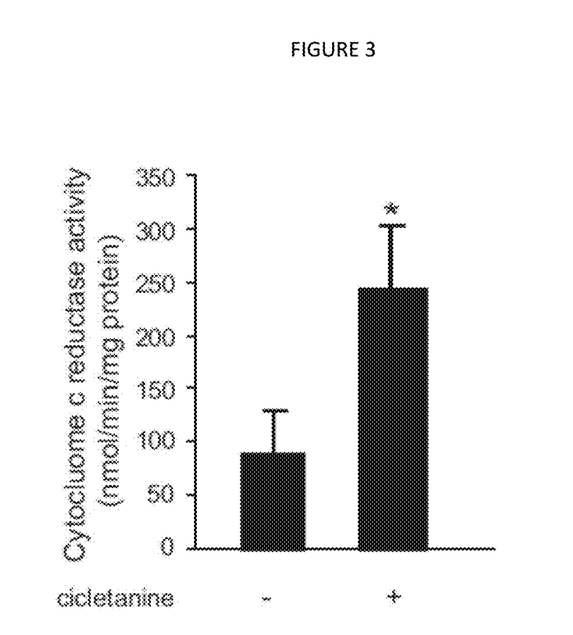
FIG. 3 is a chart that shows cicletanine potentiates eNOS cytochrome c reductase activity.

FIG. 3 shows cicletanine potentiates eNOS cytochrome c reductase activity. Sinusoidal endothelial cells were isolated from rat livers and exposed to cicletanine (100 nM) for 2 h, cell lysates were harvested, and NADPH cytochrome c reductase activity was measured as in MATERIALS AND METHODS. Cells without treatment served as a control. The rate of basal cytochrome c reductase activity and the cytochrome c reductase activity in the presence of calmodulin (CaM) are shown graphically (n=3, *P<0.01 vs. control).

Cicletanine-Induced eNOS Activity is Akt Dependent.

Figure 4:
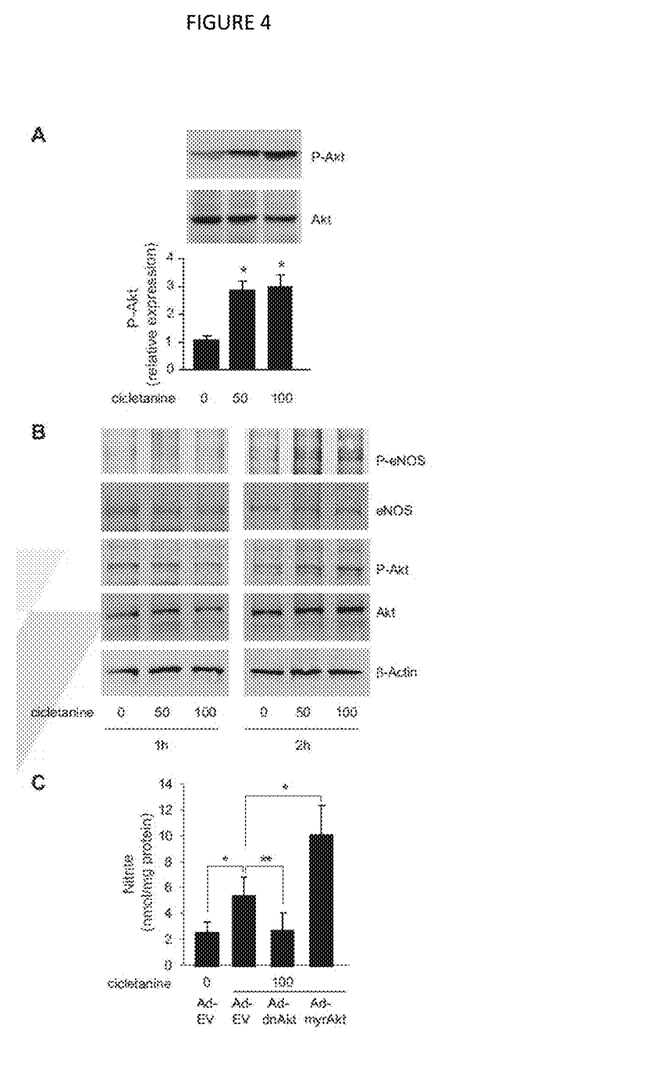
FIG. 4 comprises charts and graphics showing cicletanine-induced eNOS activity is protein kinase B (Akt) dependent.

To understand the mechanism by which cicletanine stimulates eNOS, we performed studies examining the known eNOS-signaling partner Akt. Again, cicletanine increased eNOS phosphorylation at Ser$^{1177}$ as well as Akt phosphorylation at Ser$^{473}$ without a change in total Akt expression (FIG. 4, A and B). To determine whether eNOS phosphorylation by cicletanine was Akt dependent, we transduced sinusoidal endothelial cells with Ad-myrAkt, Ad-dnAkt, or Ad-EV for 24 h and exposed cells to cicletanine (100 nM) for an additional 2 h. Cicletanine stimulated nitrite production while the dominant active Akt further increased it and the dominant negative Akt blocked cicletanine's effects (FIG. 4C). These data suggest that cicletanine's mechanism of action requires Akt signaling.

FIG. 4 shows cicletanine-induced eNOS activity is protein kinase B (Akt) dependent. A: sinusoidal endothelial cells were isolated from rat livers and were exposed to 50 or 100 nM cicletanine for 2 h, and cell lysates were harvested and subjected to immunoblotting to detect phospho (Ser$^{473}$)- and total Akt. In the graph shown on bottom, bands corresponding to phospho-Akt were quantified (n=3, *P<0.01 vs. control). B: sinusoidal endothelial cells were exposed to 50 or 100 nM cicletanine for 1 or 2 h, and cell lysates were harvested and subjected to immunoblotting to detect phospho-eNOS, total eNOS, phospho-Akt (Ser$^{473}$), total Akt, and β-actin. Blots representative of 3 others are shown. C: normal sinusoidal endothelial cells were infected with adenovirus (Ad, multiplicity of infection 250) encoding constitutively active Akt (Ad-myrAkt), dominant-negative Akt (AddnAkt), or an empty vector (Ad-EV) for 24 h before exposure to cicletanine (100 nM) for an additional 2 h. Conditioned medium was harvested, and nitrite levels were measured and presented in the graph; medium from cells treated with Ad-EV alone served as a control (n=3, *P<0.05 and **P<0.01 vs. control).

Figure 5:
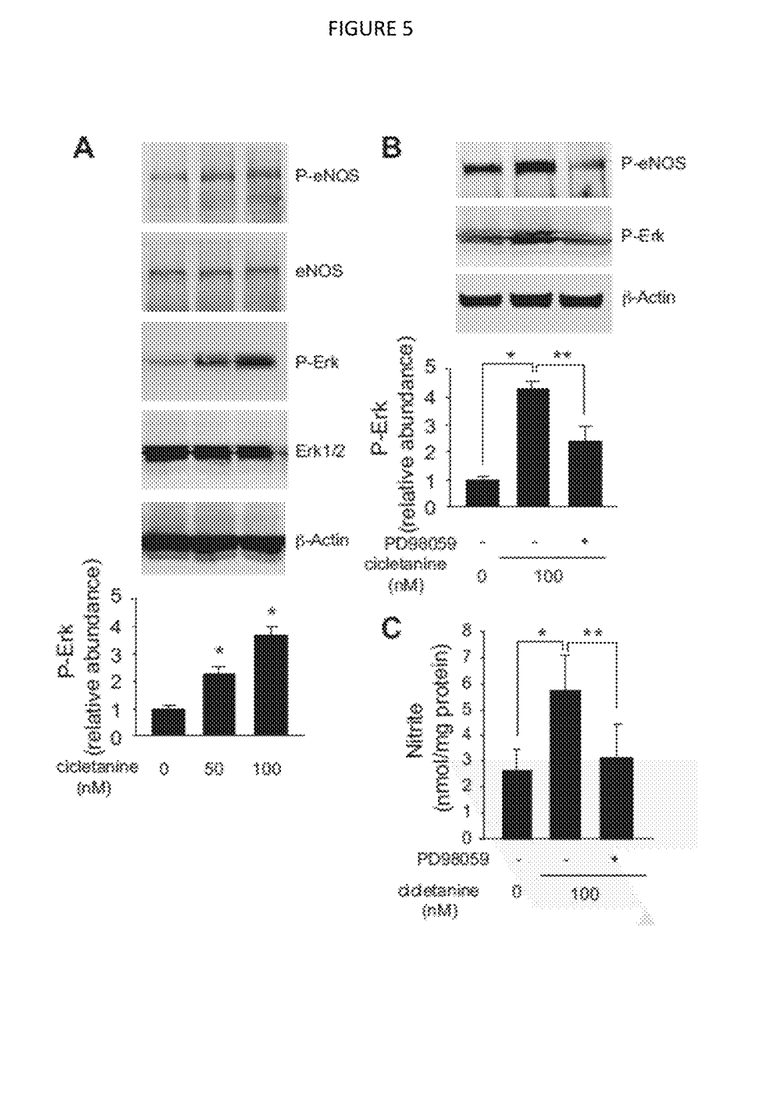
FIG. 5 comprises charts and graphics showing cicletanine-induced eNOS activity is Erk dependent.

Erk activation is involved in cicletanine-induced eNOS activity. We also explored the possibility that eNOS activation induced by cicletanine involved the MAP kinase signaling partners, including Erk1 and Erk2. First, we examined the relationship between Erk and eNOS phosphorylation. We found that phosphorylation of Erk and eNOS was increased in a dose-dependent manner after exposure of sinusoidal endothelial cells to cicletanine for 2 h (FIG. 5A). Additionally, the Erk inhibitor PD-98059 blocked cicletanine-induced eNOS phosphorylation (FIG. 5B) and NO production (FIG. 5C).

FIG. 5 shows cicletanine-induced eNOS activity is Erk dependent. A: sinusoidal endothelial cells were isolated from rat livers and were exposed to 50 or 100 nM cicletanine for 2 h, and cell lysates were subjected to immunoblotting to detect phospho-eNOS, total eNOS, phospho-Erk, total Erk1/2, and β-actin. In the graphs shown on bottom, bands corresponding to phospho-Erk were quantified (n=3, *P<0.05 vs. control). B: sinusoidal endothelial cells as in A were pretreated with the MAP kinase inhibitor PD-98059 (10 μM) for 30 min and then stimulated with cicletanine (100 nM) for an additional 2 h; eNOS and Erk phosphorylation were detected by immunoblotting. In the graph shown on bottom, bands corresponding to phospho-Erk were quantified (n=3, *P<0.01 vs. no cicletanine control, **P<0.005 vs. cicletanine control). C: conditioned supernatants from cells as in B were collected, and nitrite levels were measured (n=3, *P<0.05 vs. no cicletanine control, **P<0.01 vs. cicletanine control).

Cicletanine Stimulates eNOS Activity in Injured Sinusoidal Endothelial Cells.

Figure 6:
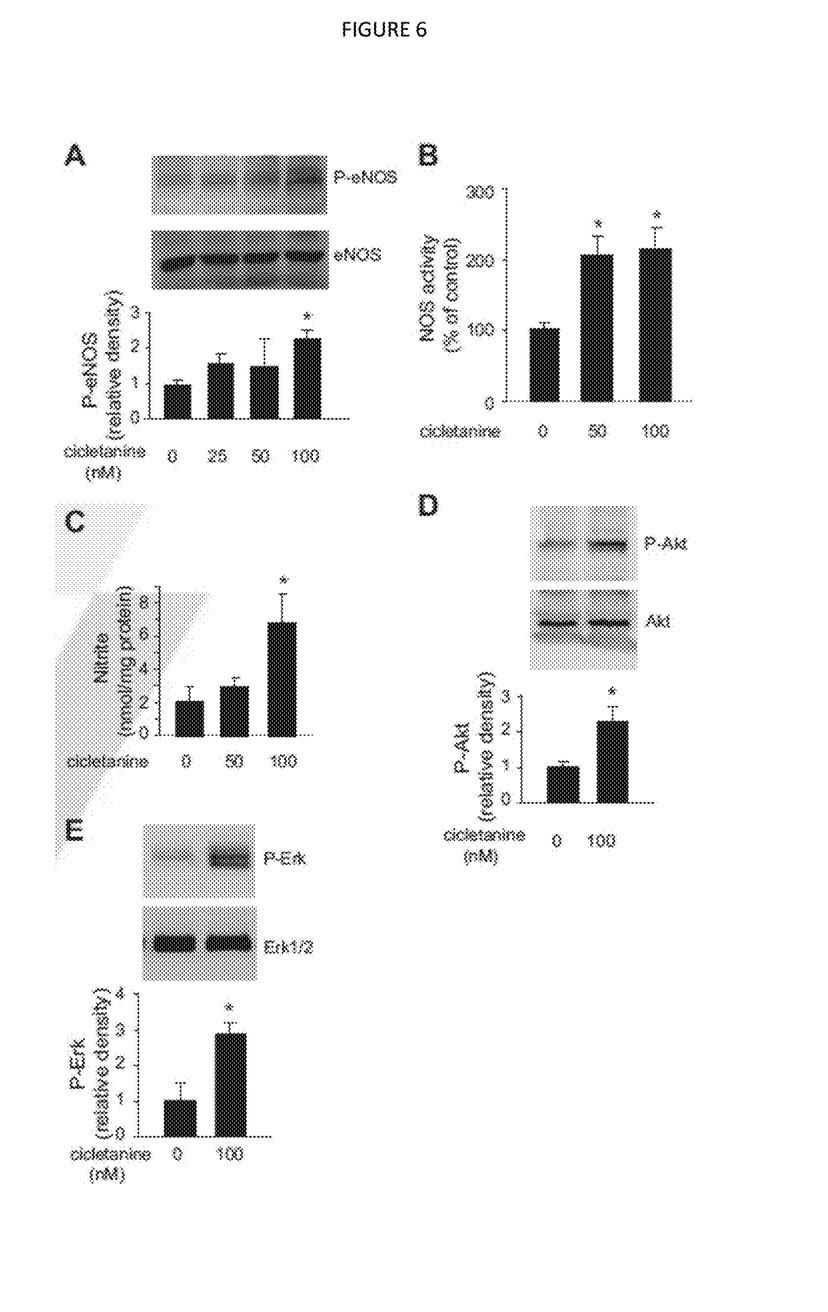
FIG. 6 comprises charts and graphics showing effects of cicletanine in injured sinusoidal endothelial cells.

We have previously shown that Akt phosphorylation and eNOS activity is reduced after liver injury and in portal hypertensive rats and mice. We next tested whether cicletanine could rescue the abnormal endothelial cell/eNOS phenotype typical of liver injury. Cicletanine restored eNOS phosphorylation to above basal levels in sinusoidal endothelial cells injured by bile duct ligation (note that there is little to no phosphorylated eNOS in unstimulated cells; FIG. 6A), concomitant with an increase in eNOS activity [eNOS activity in injured sinusoidal endothelial cells is significantly reduced compared with that from normal endothelial cells; FIG. 6B] and nitrite production (FIG. 6C). Cicletanine also restored Akt phosphorylation to above normal levels (FIG. 6D) and increased Erk1/2 phosphorylation (FIG. 6E).

FIG. 6 shows effects of cicletanine in injured sinusoidal endothelial cells. A: sinusoidal endothelial cells were isolated from rat livers 10 days after bile duct ligation (BDL), allowed to adhere overnight, and then exposed to the indicated concentrations of cicletanine for 2 h; cells were harvested, and cell lysates were subjected to immunoblotting to detect phospho- and total eNOS. In the graph shown on bottom, bands corresponding to phospho-eNOS were quantified (n=3, *P<0.01 vs. control). B: sinusoidal endothelial cells as in A were harvested, and NOS activity was measured in cell lysates; NOS activity was normalized to that of control cells and is presented graphically (n=3, *P<0.005 vs. control). C: conditioned medium as in A was harvested, and nitrite levels were measured as in MATERIALS AND METHODS (n=3, *P<0.05 vs. control). D and E: sinusoidal endothelial cells as in A were harvested, and cell lysates were immunoblotted to detect phospho- and total Akt and phospho- and total Erk1/2, respectively. Bands corresponding to phospho-Akt and phospho-Erk were quantitated, normalized, and shown in the lower graphs (D: n=3, *P<0.01 vs. control; E: n=3, *P<0.005 vs. control).

Cicletanine-Induced NO Inhibits Stellate Cell Contractility Via Activation of NO/Protein Kinase G.

To determine whether cicletanine-induced NO has a physiological function, we developed a coculture model in which we cultured sinusoidal endothelial cells with hepatic stellate cells, the latter of which generate considerable contractile force. We used a model in which stellate cells were cultured on thick collagen lattices; after their activation by ET-1, they contract. Cicletanine inhibited stellate cell contraction in a dose-dependent manner (FIG. 7A), consistent with a relevant physiological effect. Next, we studied protein kinase G (PKG) activation by assaying phospho-vasodilator-stimulated phosphoprotein (VASP) in stellate cells cocultured with or without sinusoidal endothelial cells. VASP, a key downstream target of the NO/cGMP signaling pathway, is a vasodilator-stimulated phosphoprotein. We found that cicletanine did not alter VASP phosphorylation in stellate cells, but it stimulated VASP phosphorylation in stellate cells cocultured with sinusoidal endothelial cells (FIG. 7B) in a dose-dependent manner and was inhibited by the eNOS inhibitor L-NAME (FIG. 7C).

Figure 7:
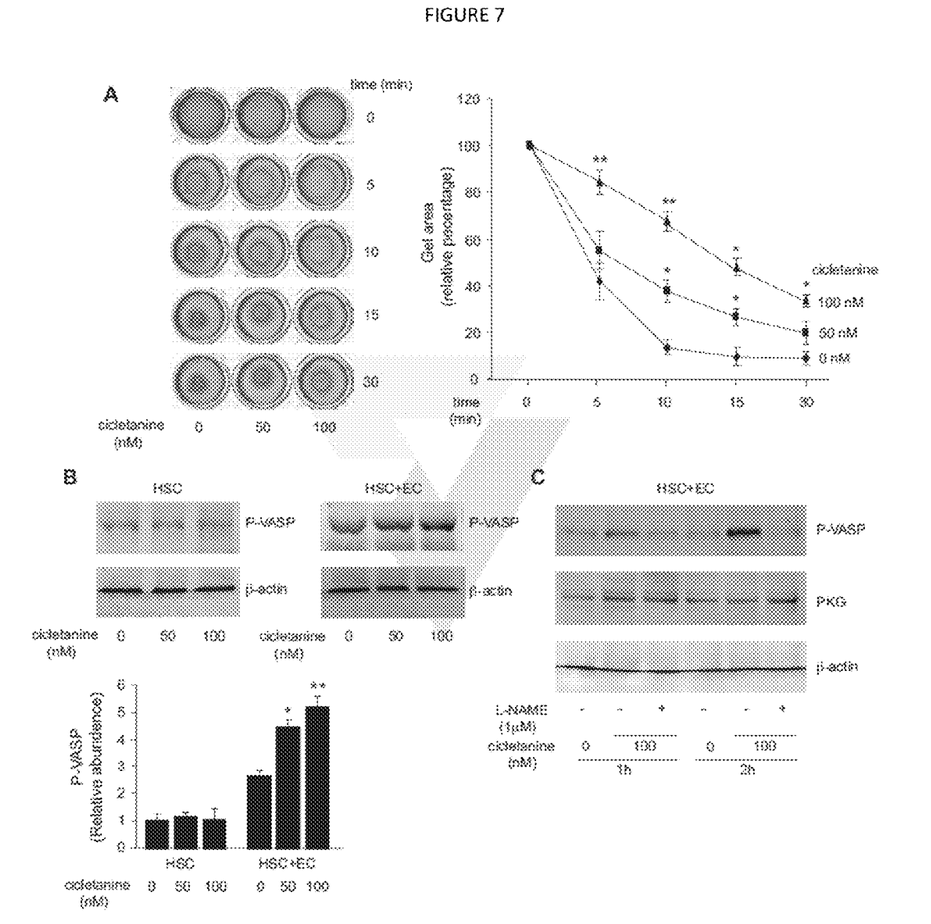
FIG. 7 charts and graphics showing cicletanine-induced nitric oxide (NO) production in sinusoidal endothelial cells causes protein kinase G (PKG) activation and stellate cell relaxation.

FIG. 7 shows cicletanine-induced nitric oxide (NO) production in sinusoidal endothelial cells causes protein kinase G (PKG) activation and stellate cell relaxation. A: hepatic stellate cells and sinusoidal endothelial cells were isolated separately from rat livers and cocultured (each at a density of 100,000 cells/lattice) on collagen lattices for 5 days as in MATERIALS AND METHODS. Cells were then serum starved overnight, exposed to 50 or 100 nM cicletanine for 2 h, and then stimulated with endothelin-1 (ET-1, 10 nM). Collagen lattices were released from their substrata, and gel contraction was measured over time. A representative experiment with images of changes in gel area at the indicated time points is shown on left. Gel areas were measured, quantified, and depicted quantitatively in the graph on the right (n=4, *P<0.05 and **P<0.001 vs. control). B: hepatic stellate cells (HSC) and sinusoidal endothelial cells (EC) were isolated, and HSC were cultured alone or cocultured (HSC+EC) as in MATERIALS AND METHODS. Cells were harvested, and cell lysates were immunoblotted to detect phospho-vasodilator-stimulated phosphoprotein (VASP) for PKG activity. HSC or HSC+EC without cicletanine served as controls. Bands corresponding to phospho-VASP were quantitated, normalized, and shown in the lower graph (n=3, *P<0.01 and **P=0.001 vs. HSC+EC control). C: cells (HSC+EC) as in B were preexposed to L-NAME (1 μM) for 4 h and then exposed to cicletanine (100 nM) for an additional 1-2 h. Phospho-VASP, PKG, and β-actin were detected in cell lysates by immunoblotting, and representative images are shown.

Cicletanine Reduces Portal Pressure In Vivo.

Figure 8:
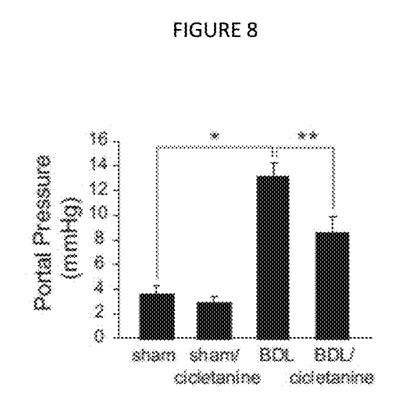
FIG. 8 is a chart showing cicletanine reduces portal pressure.

To investigate whether cicletanine may have an effect on intrahepatic relaxation in vivo, we measured portal pressure following cicletanine gavage in bile duct-ligated (BDL) mice. As expected, portal pressure was significantly elevated in BDL mice compared with sham-operated mice (FIG. 8). However, cicletanine treatment significantly reduced portal pressure after BDL. Slight and nonsignificant decreases in portal pressure were observed in sham-operated mice in response to cicletanine.

FIG. 8 shows cicletanine reduces portal pressure. Portal hypertension was induced by performing BDL in BALB/c mice; sham operations were also performed as described in MATERIALS AND METHODS. Cicletanine (5 mg·kg$^{-1}$·day$^{-1}$) or vehicle was given by gavage in a single daily dose for 10 days before portal pressure measurement (which was performed at day 28) as described in MATERIALS AND METHODS and presented graphically (n=5 for each group; *P<0.001 and **P<0.005 for differences between indicated groups).

Discussion

Figure 9:
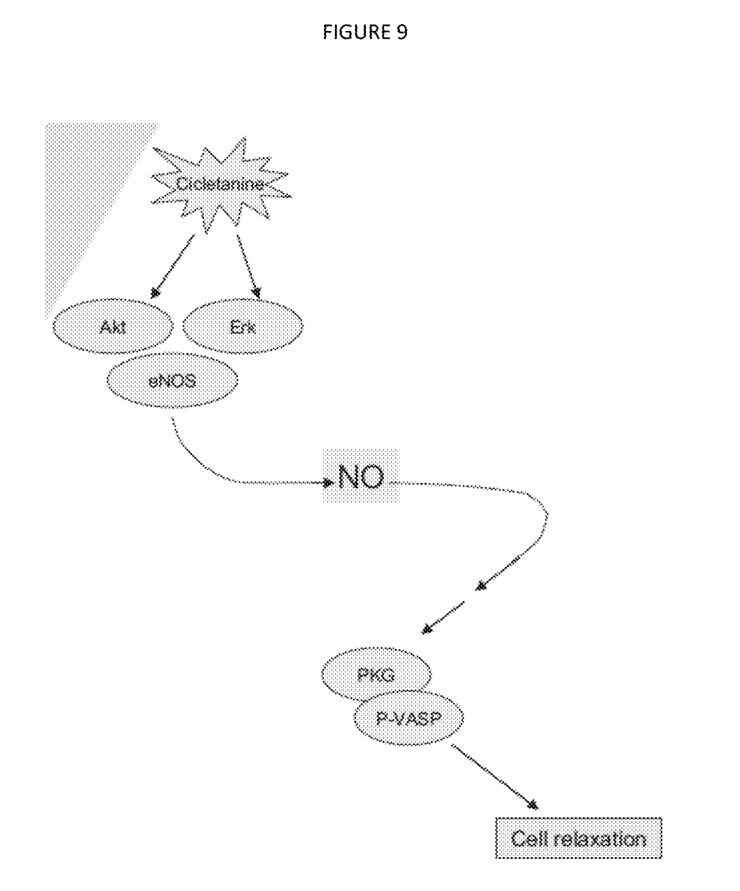
FIG. 9 shows a proposed model of cicletanine effects on sinusoidal endothelial cells.

We have shown that cicletanine directly stimulates eNOS in sinusoidal endothelial cells in a concentration- and dose-dependent fashion; the mechanism of eNOS activation appears to be linked to an Akt/Erk pathway and regulation of stellate cell contractility via the NO/PKG signaling pathway (FIG. 9). Additionally, cicletanine stimulated eNOS in injured sinusoidal endothelial cells, suggesting and we posit that it may rescue abnormal signaling pathways.

FIG. 9 shows a proposed model of cicletanine effects on sinusoidal endothelial cells. Cicletanine, a furopyridine derivative, stimulated eNOS phosphorylation in sinusoidal endothelial cells (SECs). The data suggest a dual role, including at the level of Akt-eNOS and Erk-eNOS signaling. Cicletanine-mediated NO generation via enhanced eNOS activity appears to stimulate soluble guanylate cyclase in stellate cells, which activates cGMP/PKG and (downstream) VASP, leading to stellate cell relaxation.

Our data extend previous studies by indicating that the mechanism by which cicletanine acts is by posttranslational eNOS phosphorylation and activation.

Currently, posttranslational mechanisms of eNOS activation are an area of active investigation. eNOS catalytic function is influenced by phosphorylation, acylation, and protein interactions. Because phosphorylation of eNOS at Ser$^{1177}$ by Akt is critical for activation of eNOS, we investigated the effects of cicletanine in this regard; our results clearly indicate that cicletanine activates the protein kinase Akt, leading to posttranslational activation of eNOS via phosphorylation of Ser$^{1177}$ (FIGS. 4 and 6).

The interrelationships of eNOS and MAP kinase pathways are not entirely understood. Of note, eNOS has many putative MAP kinase phosphorylation consensus binding site sequences. We inquired as to whether cicletanine stimulates Erk and thus eNOS. We found that cicletanine robustly induced Erk activation in sinusoidal endothelial cells (FIGS. 5 and 6). PD-098059, an MEK inhibitor and downstream inactivator of Erk, abolished cicletanine stimulation of Ser$^{1177}$ phosphorylation and NO generation, suggesting a role for Erk. Thus, it is proposed and we posit that cicletanine regulates eNOS in a dual pathway involving Akt and Erk.

The biochemical basis by which NOS functions is via the regulation of electron flux form NADPH through flavins in the reductase portion of NOS protein to the heme domain in the oxygenase domain and control the rate of NO synthesis. We therefore examined eNOS cytochrome c reductase activity and found that cicletanine is able to enhance the rate of cytochrome c reduction twofold more compared with no cicletanine treatment in both the basal level and CaM stimulation (FIG. 3), suggesting that cicletanine plays a critical role on the electron flux from the reductase domain to the oxygenase domain and contributes to increase NO generation in sinusoidal endothelial cells.

Portal hypertension is associated with deficient endothelial cell NO production, which results in increased intrahepatic resistance and portal pressure. Thus, providing the liver with NO is a potentially novel therapeutic strategy. Here, we found that cicletanine, which has been shown to have effects on the pulmonary endothelium, not only enhances eNOS activity in normal sinusoidal endothelial cells but also improves the reduced eNOS activity typical of injured sinusoidal endothelial cells (FIG. 6). The mechanism appears to involve enhancement of Akt-Erk-eNOS signaling in injured sinusoidal endothelial cells. Overall, our data substantially extend previous work and emphasize a mechanism involving ERK responsible for the impairment of sinusoidal endothelium-dependent NO production in injured sinusoidal endothelial cells. The data also raise the possibility that cicletanine may augment eNOS bioactivity and may be useful for treatment of portal hypertension (FIG. 9).

Human Study Example I

A racemic formulation of drug Cicletanine is administered orally, once or twice daily in doses in the range of 100 to 400 mg, to subjects suffering from cirrhosis, nonalcoholic steatohepatitis (NASH) or another liver disorder associated either with endothelial dysfunction or deactivation of protein kinase G. The drug is administered either as a first-line drug or as a drug given in addition to, or as a replacement for a previous/current drug given for cirrhosis, nonalcoholic steatohepatitis (NASH) or another liver disorder associated either with endothelial dysfunction or deactivation of protein kinase G.

When this formulation is administered to appropriate subjects (including, but not limited to those suggested above) portal blood pressure (if elevated) falls favorably and effects upon metabolic parameters (in particular, blood glucose levels, glucose tolerance, blood triglyceride levels, blood cholesterol [total, LDL and HDL] levels) are positive or remain neutral to minimal. Insulin resistance, if present, decreases. Liver enzymes, such as alanine aminotransferase (ALT) or aspartate aminotransferase (AST), if elevated, return toward normal levels.

These results indicate that the drug formulation above has favorable metabolic, vasorelaxant and organ-protective effects.

Human Study Example II

A non-racemic combination drug put into a pill or capsule or other formulation containing approximately a 1:6 ratio of (+) Cicletanine to (−) Cicletanine, with 12.5-75 mg of the (+) enantiomer of Cicletanine combined with 75-450 mg of the (−) enantiomer of Cicletanine and is administered orally, once or twice daily, to subjects suffering from cirrhosis, nonalcoholic steatohepatitis (NASH) or another liver disorder associated either with endothelial dysfunction or deactivation of protein kinase G. The drug is administered either as a first-line drug or as a drug given in addition to, or as a replacement for a previous/current drug given for cirrhosis, nonalcoholic steatohepatitis (NASH) or another liver disorder associated either with endothelial dysfunction or deactivation of protein kinase G.

When this formulation is administered to appropriate subjects (including, but not limited to those suggested above) portal blood pressure (if elevated) falls favorably and effects upon metabolic parameters (in particular, blood glucose levels, glucose tolerance, blood triglyceride levels, blood cholesterol [total, LDL and HDL] levels) are positive or remain neutral to minimal. Insulin resistance, if present, decreases. Liver enzymes, such as alanine aminotransferase (ALT) or aspartate aminotransferase (AST), if elevated, return toward normal levels.

These results indicate that the drug formulation above has favorable metabolic, vasorelaxant and organ-protective effects.

Human Study Example III

A non-racemic combination drug put into a pill or capsule or other formulation containing approximately a 3:1 ratio of (+) Cicletanine to (−) Cicletanine, with 50-300 mg of the (+) enantiomer of Cicletanine combined with 16.7-100 mg of the (−) enantiomer of Cicletanine and is administered orally, once or twice daily, to subjects suffering from cirrhosis, nonalcoholic steatohepatitis (NASH) or another liver disorder associated either with endothelial dysfunction or deactivation of protein kinase G. The drug is administered either as a first-line drug or as a drug given in addition to, or as a replacement for a previous/current drug given for cirrhosis, nonalcoholic steatohepatitis (NASH) or another liver disorder associated either with endothelial dysfunction or deactivation of protein kinase G.

When this formulation is administered to appropriate subjects (including, but not limited to those suggested above) portal blood pressure (if elevated) falls favorably and effects upon metabolic parameters (in particular, blood glucose levels, glucose tolerance, blood triglyceride levels, blood cholesterol [total, LDL and HDL] levels) are positive or remain neutral to minimal. Insulin resistance, if present, decreases. Liver enzymes, such as alanine aminotransferase (ALT) or aspartate aminotransferase (AST), if elevated, return toward normal levels.

These results indicate that the drug formulation above has favorable metabolic, vasorelaxant and organ-protective effects.

In certain applications, the mixture of furopyridine isomers (including cicletanine isomers) may be racemic or mixtures favoring either the (+) or (−) enantiomer. Ranges of non-racemic mixtures can extend from 10:1 to 1:10 of (+) enantiomer to (−) enantiomer, more preferably, 6:1 to 1:6 of (+) enantiomer to (−) enantiomer, and even more preferably, 3:1 to 1:3 of (+) enantiomer to (−) enantiomer, and even more preferably, 2:1 to 1:2 of (+) enantiomer to (−) enantiomer. In certain embodiments a twice daily administration of the medicament is found more effective than a single daily administration. Effective dosages may range from 10 to 600 mg daily, more preferably 100 to 400 mg daily, even more preferably 150 to 350 mg daily.

In summary, our data support a physiological role for the use of pharmacological agents such as cicletanine to stimulate eNOS function in sinusoidal endothelial cells, which had paracrine effects on stellate cells (FIG. 7), and additionally reduced portal pressure (FIG. 8). The data highlight the possibility that pharmacological intervention in patients with increased intrahepatic resistance and portal hypertension may be clinically feasible.

Aspects of the present invention also include the uses or substitution of furopyridines other than cicletanine, including the uses of various isomers or isomer combinations of the same in the systems, methods, techniques, and compounds described herein of the present invention. Aspects of the present invention also include combinations of and the use of combinations of furopyridines (or isomers of the same) other than cicletanine with cicletanine (or isomers of the same) in the systems, methods, techniques, and other embodiments described herein of the present invention.

While a number of preferred embodiments of the invention and variations thereof have been described in detail, other modifications and methods of using the disclosed therapeutic combinations will be apparent to those of skill in the art. Accordingly, it should be understood that various applications, modifications, and substitutions may be made of equivalents without departing from the spirit of the invention or the scope of the claims. Further, it should be understood that the invention is not limited to the embodiments set forth herein for purposes of exemplification, but is to be defined only by a fair reading of the appended claims, including the full range of equivalency to which each element thereof is entitled. The therapeutic applications may be administered via various modalities as known in the art.

Further description of the present invention is shown in the publication by co-inventors Rockey and Liu entitled "Cicletanine Stimulates eNOS Phosphorylation and NO Production via Akt and MAP kinase/Erk Signaling in Sinusoidal Endothelial Cells" published at *Am J Physiol Gastrointest Liver Physiol.* 2013 July; 305 (2):G163-71. All of the references cited herein are incorporated in their entirety by reference thereto.

What is claimed is:

1. A method of treating portal hypertension by administration of therapeutically effective amounts of cicletanine.

2. The method of 1 in which the cicletanine administered is predominately in the form of the (+) isomer of the cicletanine.

3. The method of claim 1 in which the cicletanine administered is a non-racemic mixture of cicletanine.

4. The method of claim 3 in which the cicletanine administered is a mixture that favors the (+) isomer over the (−) isomer.

5. A method of treating portal hypertension by administration of therapeutically effective amounts of a non-racemic mixture of cicletanine enantiomers in which the ratio of (+) enantiomer to (−) enantiomer is in the range of from 2:1 to 10:1.

* * * * *